US009347096B2

(12) United States Patent  (10) Patent No.: US 9,347,096 B2
Morishima et al.  (45) Date of Patent: May 24, 2016

(54) GENETIC ANALYZER

(75) Inventors: Daisuke Morishima, Tokyo (JP);
Kohshi Maeda, Tokyo (JP); Nobuyoshi Shimane, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 13/982,544

(22) PCT Filed: Jan. 23, 2012

(86) PCT No.: PCT/JP2012/000361
§ 371 (c)(1),
(2), (4) Date: Jul. 30, 2013

(87) PCT Pub. No.: WO2012/105176
PCT Pub. Date: Aug. 9, 2012

(65) Prior Publication Data
US 2013/0316441 A1  Nov. 28, 2013

(30) Foreign Application Priority Data

Jan. 31, 2011 (JP) ................................. 2011-017393

(51) Int. Cl.
*C12Q 1/68* (2006.01)
*G01N 35/00* (2006.01)
*B01L 7/00* (2006.01)

(52) U.S. Cl.
CPC ............ *C12Q 1/686* (2013.01); *G01N 35/0092* (2013.01); *B01L 7/52* (2013.01); *C12Q 1/6846* (2013.01); *C12Q 2527/107* (2013.01); *C12Q 2561/113* (2013.01)

(58) Field of Classification Search
CPC .......... B01J 19/00; B01L 7/52; C12Q 1/6846; C12Q 1/686; C12Q 2561/113; G01N 35/0092
USPC ....................................... 435/287.2
See application file for complete search history.

(56) References Cited

U.S. PATENT DOCUMENTS

| 5,525,300 | A | * | 6/1996 | Danssaert | B01L 7/52 422/552 |
| 2004/0115720 | A1 | * | 6/2004 | McWilliams et al. | 435/6 |
| 2007/0100569 | A1 | | 5/2007 | DeSimas et al. | |
| 2009/0018776 | A1 | | 1/2009 | Taylor | |
| 2009/0298129 | A1 | * | 12/2009 | Spence et al. | 435/91.2 |

FOREIGN PATENT DOCUMENTS

JP  2009-106222 A  5/2009

OTHER PUBLICATIONS

Mx3000P/Mx3005P Real Time Teiryo PCR System, Catalog, Agilent Technologies Inc., 2010.
Smart Cycler II, Catalog, Takara Bio Inc., 2009.
Japanese Office Action received in Japanese Application No. 2012-555725 dated Jun. 17, 2014.
Chinese Office Action received in Chinese Application No. 201280006973.5 dated Apr. 14, 2014.

* cited by examiner

*Primary Examiner* — Nathan Bowers
*Assistant Examiner* — Lydia Edwards
(74) *Attorney, Agent, or Firm* — Mattingly & Malur, PC

(57) ABSTRACT

A nucleic acid analysis apparatus capable of selecting an optimal analysis method for every user and improving throughput is provided. In a genetic analyzer for measuring and analyzing amplification reaction of a nucleic acid in real time, an amplification curve is analyzed and a user can select conditions for terminating the amplification reaction upon detection of amplification. Further, a user can select conditions for selecting next processing after termination of the amplification reaction. A user can select, in situ, conditions for terminating the amplification reaction and conditions for selecting next processing upon detection of amplification and after the termination of amplification reaction. Alternatively, conditions for terminating the amplification reaction and conditions for selecting the next processing are registered previously and processing is performed automatically upon detection of amplification and after termination of the amplification reaction.

20 Claims, 10 Drawing Sheets

○ AMPLIFICATION REACTION IS TERMINATED INSTANTLY
○ AMPLIFICATION REACTION IS CONTINUED TILL MEASUREMENT COMPLETION TIME AND THEN TERMINATED
● AMPLIFICATION REACTION IS CONTINUED FOR [   ] SECONDS AND THEN TERMINATED     600

[ OK ]

(B)

601            602

Ct VALUE HAS BEEN DETECTED. (SAMPLE ID 123456-001)
PLEASE SELECT CONDITION FOR TERMINATING AMPLIFICATION REACTION.

● AMPLIFICATION REACTION IS TERMINATED INSTANTLY
○ AMPLIFICATION REACTION IS CONTINUED TILL MEASUREMENT COMPLETION TIME AND THEN TERMINATED
○ AMPLIFICATION REACTION IS CONTINUED FOR [   ] SECONDS AND THEN TERMINATED

[ OK ]

(C)

Ct VALUE HAS BEEN DETECTED. (SAMPLE ID 123456-001)
PLEASE SELECT CONDITION FOR TERMINATING AMPLIFICATION REACTION.

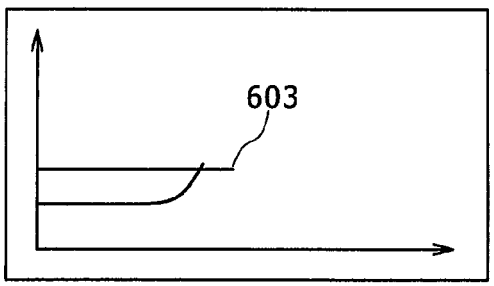

603

● AMPLIFICATION REACTION IS TERMINATED INSTANTLY
○ AMPLIFICATION REACTION IS CONTINUED TILL MEASUREMENT COMPLETION TIME AND THEN TERMINATED
○ AMPLIFICATION REACTION IS CONTINUED FOR [   ] SECONDS AND THEN TERMINATED

○ HRM ANALYSIS PROCESSING IS PERFORMED
● THERMAL DENATURATION PROCESSING IS PERFORMED
○ REACTION VESSEL IS DISCARDED

[ OK ]

(B)

800　　　　　　　　　　　801

PLATEAU HAS BEEN DETECTED.　(SAMPLE ID 123456-001)
PLEASE SELECT THE NEXT PROCESSING.

● HRM ANALYSIS PROCESSING IS PERFORMED
○ THERMAL DENATURATION PROCESSING IS PERFORMED
○ REACTION VESSEL IS DISCARDED

[ OK ]

(C)

PLATEAU HAS BEEN DETECTED (SAMPLE ID 123456-001)
PLEASE SELECT THE NEXT PROCESSING.

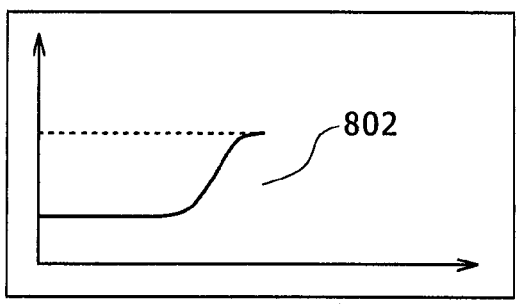

● HRM ANALYSIS PROCESSING IS PERFORMED

○ THERMAL DENATURATION PROCESSING IS PERFORMED

○ REACTION VESSEL IS DISCARDED

| RESULT OF AMPLIFICATION DETECTION | NEXT PROCESSING CONDITION |
|---|---|
| ONLY Ct VALUE IS DETECTED | THERMAL DENATURATION PROCESSING ▽ |
| PLATEAU IS DETECTED | HRM ANALYSIS PROCESSING ▽ |
| AMPLIFICATION IS NOT DETECTED | DISCARDING PROCESSING ▽ |

REACTION VESSEL ID 123456-001   SETTING OF ANALYSIS CONDITIONS (1000)

SELECTION OF CONDITION FOR AMPLIFICATION DETECTION

○ Ct VALUE DETECTION IS DEFINED AS AMPLIFICATION
● PLATEAU DETECTION IS DEFINED AS AMPLIFICATION

CONDITION FOR TERMINATING AMPLIFICATION REACTION

○ AMPLIFICATION REACTION IS TERMINATED INSTANTLY
○ AMPLIFICATION REACTION IS CONTINUED TILL COMPLETION OF MEASUREMENT TIME AND THEN TERMINATED
● AMPLIFICATION REACTION IS CONTINUED FOR [ 120 ] SECONDS AND THEN TERMINATED.

| RESULT OF AMPLIFICATION DETECTION | NEXT PROCESSING CONDITION |
|---|---|
| ONLY Ct VALUE IS DETECTED | THERMAL DENATURATION PROCESSING ▽ |
| PLATEAU IS DETECTED | HRM ANALYSIS PROCESSING ▽ |
| AMPLIFICATION IS NOT DETECTED | DISCARDING PROCESSING ▽ |

[ OK ]   [ Cancel ]

GENETIC ANALYZER

TECHNICAL FIELD

The present invention relates to a genetic analyzer of amplifying and inspecting a target nucleic acid.

BACKGROUND ART

As a method of inspecting infectious diseases or genes, a nucleic aid amplification technique of amplifying and detecting nucleic acids has been utilized. An example of the amplification technique is a PCR (Polymerase Chain Reaction) method. The PCR method is a method of repeating temperature change (temperature cycle) to reaction solutions containing target nucleic acids to selectively amplify specific base sequences.

As a method of detecting an amplification reaction by the PCR method in real time for analyzing a target nucleic acid quantitatively, there is a real time PCR method. In the existent real time PCR apparatus, identical temperature cycle is started to perform amplification reaction for a plurality of reaction solutions simultaneously.

In the existent nucleic acid inspection, the ratio of the step of measuring the amplification reaction of a nucleic acid in which real time PCR and fluorescence measurement are repeated in the analysis period is higher than that for the sample preparation step to result in a significant effect on the analytical processing speed.

Then, there is also a real time PCR apparatus of a configuration in which the detection of amplification is judged before a predetermined amplification completion time and a reaction solution after termination of the amplification reaction (after detection of amplification) is discharged from a region to perform the amplification reaction and supplies a fresh reaction solution is supplied to the region to perform the amplification reaction.

Further, in recent years, there has been known a method of analyzing a genetic polymorphism such as SNPs or mutation by using a reaction solution after the PCR amplification reaction which is referred to as Melting analysis or HRM analysis (High Resolution Melting Analysis).

CITATION LIST

Patent Literature

Patent Literature 1: Japanese Unexamined Patent Application Publication No. 2009-106222

SUMMARY OF INVENTION

Technical Problem

In the method described in the Patent Literature 1, detection of amplification is judged by detection of a plateau. However, as a method of detecting amplification, means capable of judging amplification at an earlier stage than the detection of the plateau such as detection of Ct value also exists. Accordingly, while there are a plurality of conditions for judging the amplification, if the judgment for the inspection of amplification is defined uniformly, there was a problem that a user cannot select an optimal condition for the termination of amplification depending on a sample to be measured.

On the other hand, processing after the amplification reaction has also become varied including, for example, HRM analysis. In the existent apparatus, Melting analysis or HRM analysis has been performed uniformly after lapse of a predetermined measurement completion time. However, since the Melting analysis or HRM analysis is not necessary for the reaction solution in which the amplification could not be inspected to cause loss in the analysis. Further, depending on the sample to be measured, Melting analysis or HRM analysis is sometimes unnecessary. Accordingly, there has been an increasing demand for a nucleic acid analyzing apparatus capable of changing the processing after the amplification reaction in accordance with the result of the amplification reaction or the necessity of a user.

The present invention has been achieved in view of the foregoings and it intends to provide a genetic analyzer capable of selecting an optimal analysis method depending on users and improving throughput.

Solution to Problem

For solving the problems described above, a nucleic acid analyzing apparatus of the invention is characterized in that reaction of amplifying a nucleic acid is measured and analyzed in real time, detection of amplification is judged before a predetermined measurement completion time and a user can select conditions for terminating the amplification reaction when amplification is detected.

Since the user can select the conditions for terminating the amplification reaction after detection of amplification, throughput can be improved in accordance with the measurement data required for the user.

Further, the present invention is characterized in that a user can select conditions for selecting the next processing after termination of the amplification reaction.

Since the user can select the next processing after the termination of the amplification reaction, throughput can be improved by performing only the necessary next processing in accordance with the sample to be measured and analysis conditions.

Further, the invention is characterized in that the reaction for amplifying a nucleic acid is measured and analyzed in real time, detection of amplification is judged before a predetermined measurement completion time, and a user can select conditions for terminating the amplification reaction and conditions for selecting the next processing for every result of amplification reaction when the amplification is detected.

Since the user can select the conditions for terminating the amplification reaction after detection of amplification, the throughput can be improved in accordance with the measured data necessary for the user and, since the user can select the next processing in accordance with the result of amplification, the throughput can be improved by performing only the necessary next processing in accordance with a sample to be measured, analysis conditions, and a necessary result.

Further, the genetic analyzer according to the invention is characterized by having an amplification detection mechanism provided with holding units having a plurality of temperature control blocks each holding at least one reaction vessel containing a reaction solution, and a temperature control device disposed to each of the plurality of temperature control blocks and controlling the temperature of the reaction solution, thereby providing the processing of independent operation for terminating the amplification reaction described above or the next processing after termination of the amplification reaction described above for each temperature control block.

By holding a plurality of temperature control blocks controlled individually, processing operation individually optimal to samples to be measured and analysis conditions can be performed and throughput can be improved.

Advantageous Effects of Invention

According to the nucleic acid analysis apparatus of the invention, since the conditions for terminating the amplification reaction can be selected, an operation for terminating the amplification reaction optimal to a user can be performed and the throughput can be improved.

Further, since the conditions for selecting the next processing after termination of the amplification reaction can be selected, an analysis operation optimal to a user can be performed.

Further, when the analysis method is previously selected and registered in the apparatus, the apparatus can automatically perform an optimal analysis operation and throughput can be improved.

Further, in an apparatus that holds a plurality of temperature control blocks controlled individually, optimal processing operation can be performed individually and the throughput can be improved.

BRIEF DESCRIPTION OF DRAWINGS

FIG. 6 is a view for explaining a screen for conditions of terminating amplification reaction in the first embodiment.

FIG. 8 are views explaining a screen of selecting the next processing in a second embodiment.

FIG. 9 is a view for explaining a screen for selecting next processing for every result of detection of amplification in a third embodiment.

FIG. 10 is a view for explaining setting of analysis condition on every reaction vessel in the third embodiment.

DESCRIPTION OF EMBODIMENTS

One of best embodiments for practicing the invention is to be described with reference to the drawings.

Figure 1:
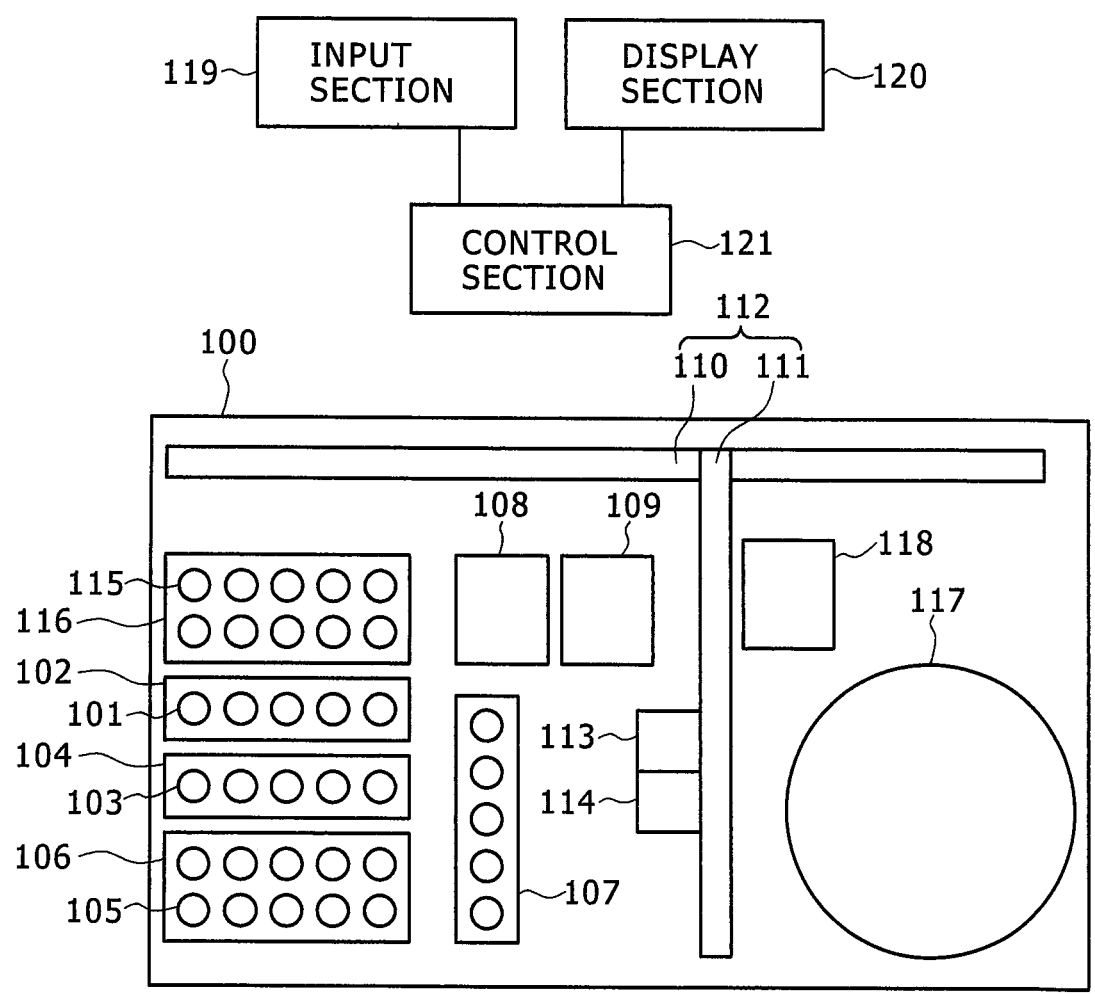
FIG. 1 is an entire schematic configurational view of a nucleic acid analysis apparatus.

FIG. 1 illustrates an entire configuration of a genetic analyzer 100 of the present invention. The genetic analyzer 100 is provided with a plurality of sample vessels 101 each accommodating a sample containing a nucleic acid as a target for amplification processing, a sample vessel rack 102 accommodating the plurality of sample vessels 101, a plurality of reagent vessels 103 accommodating various reagents to be added to the samples, a reagent vessel rack 104 accommodating a plurality of the reagent vessels 103, reaction vessels 105 for mixing the sample and the reagent, a reaction vessel rack 106 accommodating a plurality of unused reaction vessels 105, a reaction solution controlling position 107 for accommodating the unused reaction vessels 105 for dispensing the sample and the reagent from each of the sample vessels 101 and the reagent vessels 103 to the reaction vessels 105, a capping unit 108 for tightly closing the reaction vessels 105 containing the reaction solution as a liquid mixture of the sample and the reagent by a cap member (not illustrated), and a stirring unit 109 for stirring the reaction solution contained in the tightly closed reaction vessel 105.

Further, the genetic analyzer 100 is provided with a robot arm device 112 having an X axis 110 of a robot arm disposed over the genetic analyzer 100 so as to extend in the direction of the X axis (right and left direction in FIG. 1) and a Y axis 111 of a robot arm disposed so as to extend in the direction of the Y axis (vertical direction in FIG. 1) and disposed movably to the X axis 110 of the robot arm in the direction of the X axis, a gripper unit 113 disposed movably to the Y axis 111 of the robot arm in the direction of the Y axis for gripping the reaction vessel 105 and transporting the vessel to each of the sections in the genetic analyzer 100, a dispensing unit 114 disposed movably to the Y axis 111 of the robot arm in the direction of the Y axis, sucking a sample in the sample vessel 101 and a reagent in the reagent vessel 103 and discharging (dispensing) them to the controlling reaction vessel 105 disposed to the reaction solution conditioning position 107, nozzle chips 115 each attached to a portion of the dispensing unit 114 that is in contact with the sample or the reagent, a nozzle chip rack 116 accommodating a plurality of unused nozzle chips 115, a nucleic acid amplification device 117 for conducting processing of nucleic acid amplification and detecting fluorescence to a reaction solution contained in the reaction vessel 105 in the course of amplification, and a discarding box 118 for discarding the nozzle chips 115 after use and the reaction vessels 105 after use (after inspection), and a control section 121 having an input section 119 such as a keyboard and a mouse and a display unit 120 such as a liquid crystal monitor and controlling the operation of the entire genetic analyzer 100 including the nucleic acid amplification device 117.

Each of the sample vessels 101 is administrated by identification information such as a bar code for every contained sample and administrated by position information such as a coordinate allocated to each of the positions of the sample vessel rack 102. In the same manner, each of the reagent vessels 103 is administrated by identification information such as a bar code for every contained reagent and administrated by positional information such as a coordinate allocated to each of the positions of the reagent vessel rack 104. The identification information and the positional information are previously registered in the control section 121 and administrated. Further, each of the reaction vessels 105 is also administrated in the same manner by the identification information and the positional information.

The control section 121 includes at least an analysis planning section for planning analysis operation in accordance with analysis conditions which are predetermined by the genetic analyzer and designated through the display section 120, an analysis performing section for controlling each of the mechanisms in accordance with the analysis planning, and a data processing section for administrating fluorescence inspection data, etc. for every reaction vessel.

Figure 2:
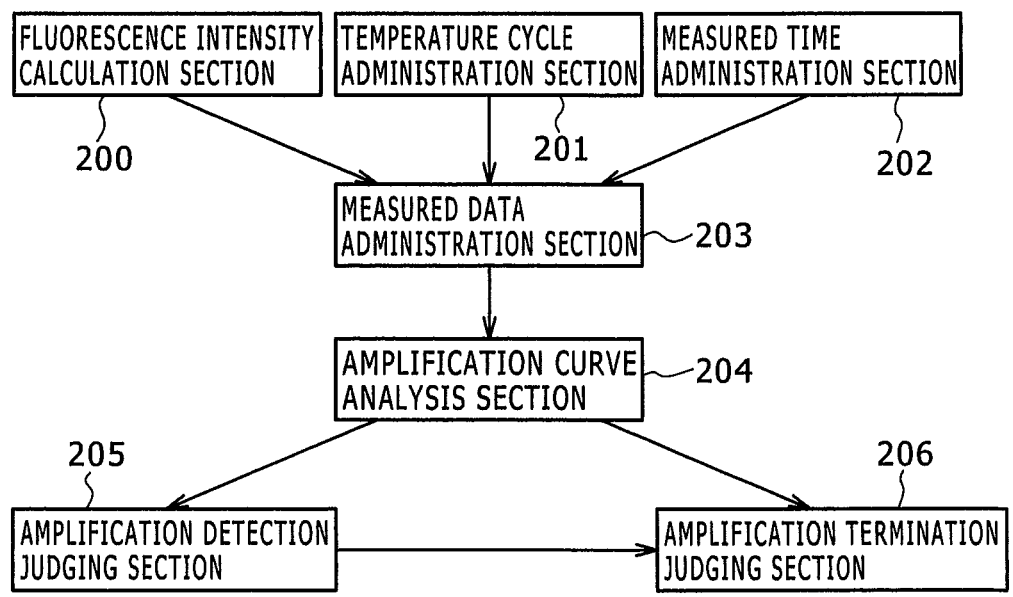
FIG. 2 is a block diagram showing a function of a control section of the nucleic acid analysis apparatus.

FIG. 2 illustrates a block diagram for a data processing section. The data processing section includes, at least, a fluorescence intensity calculation section 200 for calculating the intensity of measured fluorescence data, a temperature cycle administration section 201 for administrating the temperature cycle for every temperature control mechanism, a measurement time administration section 202 for administrating the lapse of time in analysis, a measured data administration section 203 for administrating the data of the fluorescence intensity calculation section 200, the temperature cycle control section 201, and the measurement time administration section 202 for every measured sample, as well as an amplification curve analysis section 204, an amplification inspection judging section 205, and an amplification termination judging section 206. The amplification curve analysis section 204 acquires an amplification curve from the measurement data administration section 203 to calculate a Ct value and a plateau. The amplification detection judging section 205 judges detection of nucleic acid amplification for every amplification curve in accordance with analysis conditions based on the calculated information for the Ct value and the plateau calculated by the amplification curve analysis section 204. The amplification terminating judging section 206 judges the termination of the amplification reaction based on the information on the calculation of the Ct value and the plateau calculated by the amplification curve analysis section 204, information on the temperature cycle, information on the amplification detection time, and the result of judgment for the detection of nucleic acid amplification of the amplification detection judging section 205. The information of judging the amplification detection in the amplification detection judging section 205 and the information of judging the termination of the amplification reaction in the amplification detection judging section 205 are transmitted to an analysis planning section (not illustrated) and analysis is replanned optionally.

Figure 3:
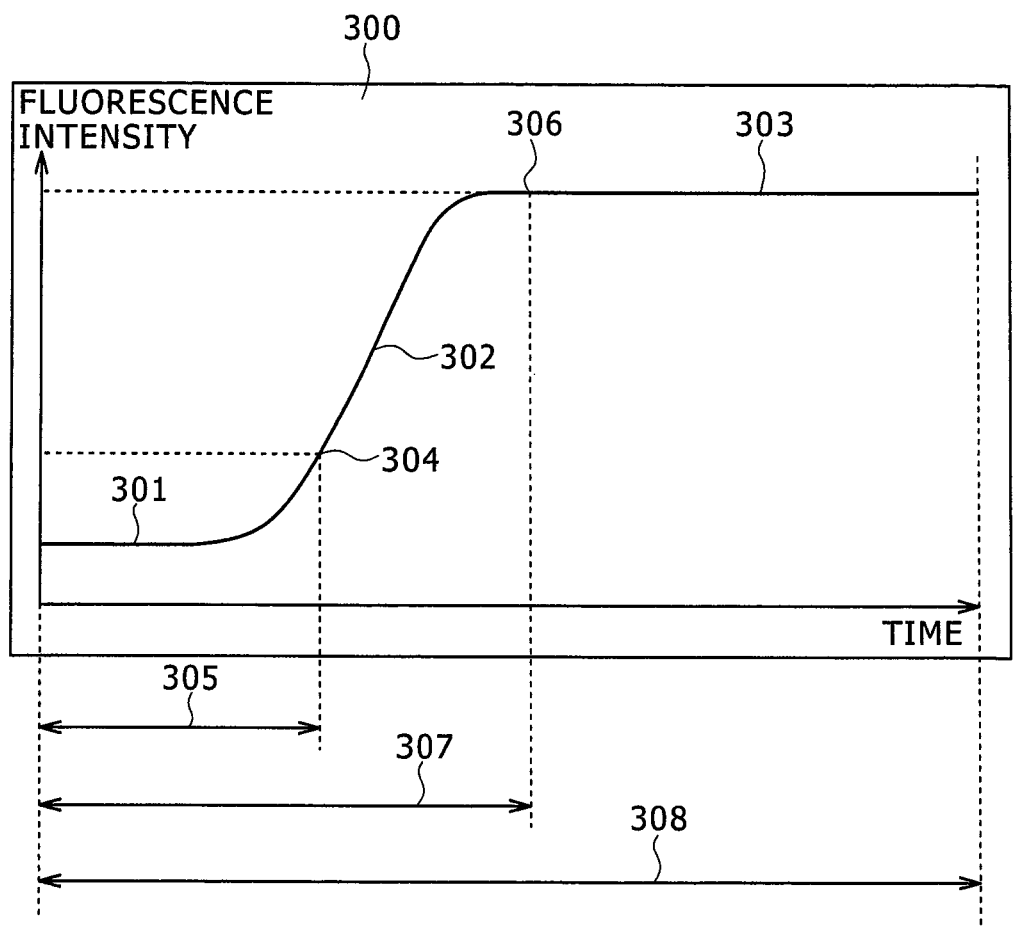
FIG. 3 is a graph showing an example of an amplification curve.

FIG. 3 illustrates an example of measured data for amplification reaction of a nucleic acid. Generally, the abscissa represents lapse of time (or number of temperature cycles) and the ordinate represents fluorescence intensity.

An amplification curve 300 includes a lag phase 301, an exponential phase 302, and a stationary phase 303. The lag phase 301 is sometimes also referred to as a base line or a base line region. The stationary phase 303 is sometimes referred to also as a plateau or a plateau region.

Naturally, when the nucleic amplification reaction does not occur till the measurement completion time 308, there is a case where only the lag phase 301 is observed, or a case where the measurement completion time 308 has been lapsed in the exponential phase 302 and the stationary phase 303 is not observed.

The measurement completion time is identical with a temperature cycle completion timing after repeating temperature change (temperature cycle) by a predetermined number of times.

Such an amplification curve 300 includes a transition region 304 between the lag phase 301 and the exponential phase 302. The transient region 304 is also referred to as a cycle threshold value (Ct value) or an elbow value. Further, the amplification curve 300 includes a transition region 306 between the exponential phase 302 and the stationary phase 303. The transition region 306 is a plateau detection point. Amplification of a nucleic acid can be judged by the Ct value detection time 305 and the plateau detection time 307.

Figure 4:
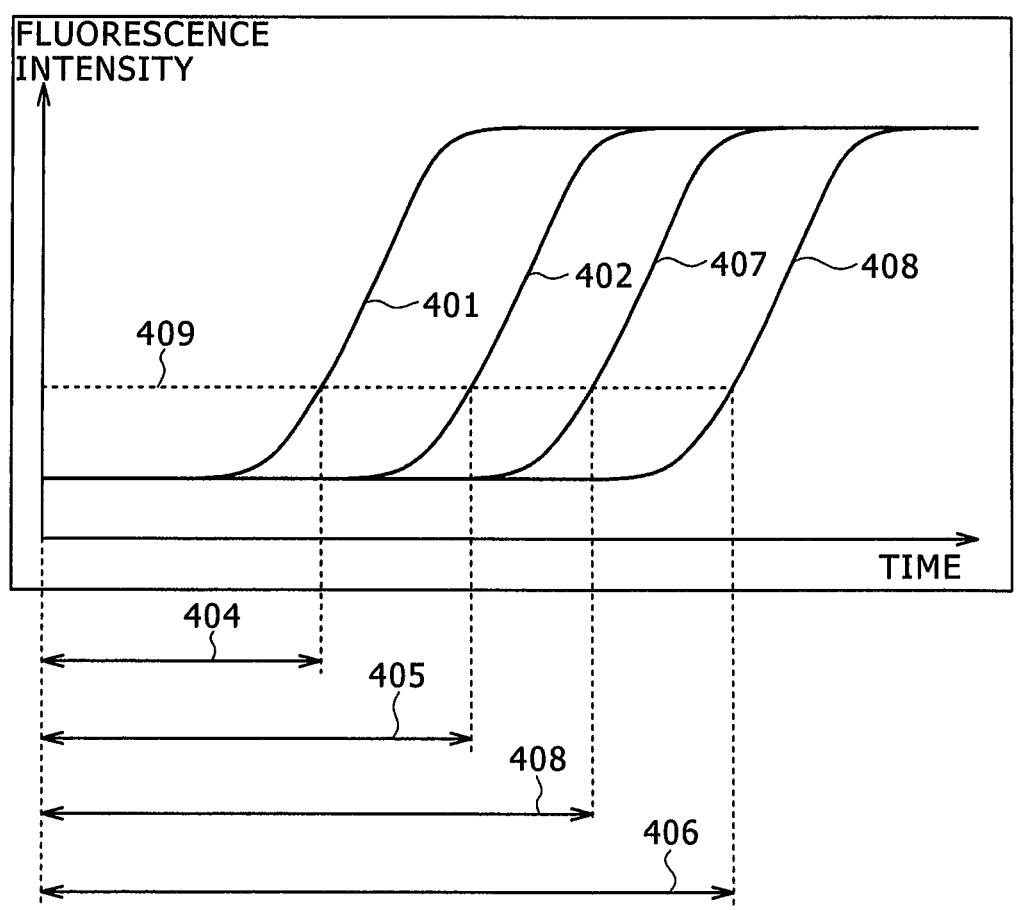
FIG. 4 is a graph showing a relation between a number of initial of copies a nucleic acid and an amplification curve.

Further, in the nucleic acid amplification curve, as the number of initial copies of the nucleic acid is larger upon starting amplification, the curve reaches the exponential phase and the stationary phase in a shorter time. Accordingly, when nucleic acid amplification curves are obtained by using standard samples diluted stepwise, amplification curves 401 to 403 are obtained in the order where the number of initial copies of the nucleic acid is larger as shown in FIG. 4. The number of initial copies of the nucleic acid contained in an unknown sample can be identified by comparing the Ct value detection times 404 to 406 for detecting the Ct value 409 of the amplification curves 401 to 403 with the Ct value detection time 408 of the amplification curve 407 of the unknown sample. Naturally, the number of initial copies of the nucleic acid can be identified also by using the plateau detection time in addition to the Ct value detection time 404.

First Embodiment

As described above, the detection time for the Ct value or the plateau is extremely important in the analysis of the nucleic acid amplification curve. On the other hand, measured data on the stationary phase after detection of the Ct value or the plateau is sometimes unnecessary depending on a user. In such a case, if the amplification reaction is continued till the measurement completion time, this lowers the throughput of the entire genetic analyzer.

In view of the above, in this embodiment, presence or absence of amplification is judged before a predetermined measurement completion time and, when amplification is detected, conditions for terminating the amplification reaction is displayed on a screen, so that a user can select conditions of terminating the amplification reaction.

Figure 5:
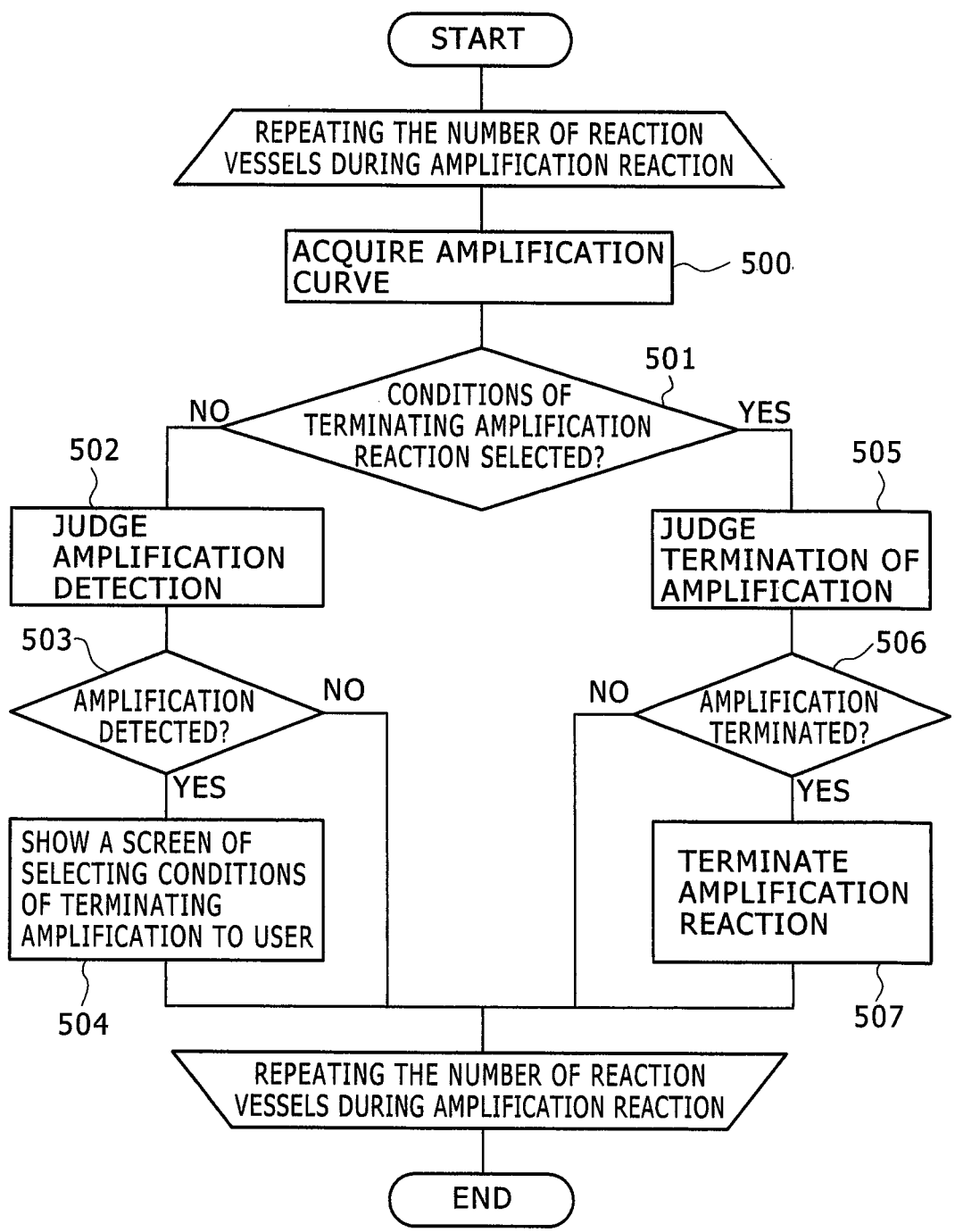
FIG. 5 is a view illustrating a flow chart in the processing of a first embodiment.

FIG. 5 illustrates a process flow of this embodiment in the control section 121. In the flow, processing is preferably performed to all of the reaction vessels during amplification reaction for every measurement period for detection of fluorescence. Processing, for example, for every predetermined cycle or processing for every cycle to a portion of the reaction vessels during amplification reaction is also possible.

In the flow, an amplification curve is at first acquired at step 500. For the amplification curve used herein, all of the fluorescence data up to the processing may be used, or only a portion of it may be used. Then, at step 501, it is judged whether conditions for terminating the amplification reaction have been selected or not. If it has not yet been selected, the flow goes to step 502, and if it has already been selected, the flow goes to step 505. At step 502, the amplification curve is analyzed and the detection of amplification is judged. At step 503, when amplification is detected, the flow goes to a step 504 in accordance with the result of judgment at step 502 and provides a screen to a user for selecting conditions of terminating the amplification reaction. In this screen, when the conditions for terminating the amplification reaction are selected, the conditions of terminating the amplification reaction is selected at step 501. Depending on the selected conditions, judgment for the detection of amplification may be changed without selecting the conditions for terminating the amplification reaction. Further, the selected conditions for terminating the amplification reaction is used in the judgment for terminating the amplification at a step 505.

Then, at step 505, the amplification curve is analyzed and termination of amplification is judged. At step 506, the flow goes to step 507 when the amplification is to be terminated in accordance with the result of judgment at step 505 and the amplification reaction of the reaction vessel is terminated.

FIG. 6(A) illustrates an example of display on a screen for selecting conditions for terminating the amplification reaction. The display screen displays conditions for terminating the amplification reaction, for example, that the amplification reaction is to be terminated instantly, the amplification reaction is continued till the completion of the measurement time and then terminated, or the amplification reaction is continued for a desired time and then terminated, so that a user can select a desired terminating condition. Further, it is preferably configured to have an input area 600 in the screen for inputting a desired time to continue the amplification reaction. While the desired time is displayed on the unit of second in FIG. 6(A), a condition equivalent to the time such as desired number of temperature cycles, number of measurement, etc. may also be used as the condition.

Other examples of the condition for terminating the amplification reaction include display of a selection screen again after lapse of the desired time. Alternatively, the conditions for terminating the amplification reaction upon detection of the Ct value may also include such an option that the amplification reaction is terminated after the detection of the plateau, or the screen for selecting the conditions for terminating the amplification reaction is displayed again after the detection of the plateau.

As a more preferred embodiment, as shown in FIG. 6 (B), an amplification detection condition 601 or a sample ID 602 may be displayed. In addition, sample information, reagent information, etc. may be displayed or referred to so long as the information belongs to the relevant reaction vessel.

Further, as shown in FIG. 6(C), an amplification reaction curve 603 may also be displayed. Further, it is preferred that the amplification reaction curve 603 can be displayed on an enlarged or reduced scale. It is preferred that the maximum value on the abscissa of the amplification reaction curve 603 is defined as a measurement completion time, so that a user can recognize the amplification curve and the remaining time up to the completion of measurement. Alternatively, a remaining time till the completion of measurement may be displayed directly. Such information provides user a reference when selecting the conditions for terminating the amplification reaction.

Figure 7:
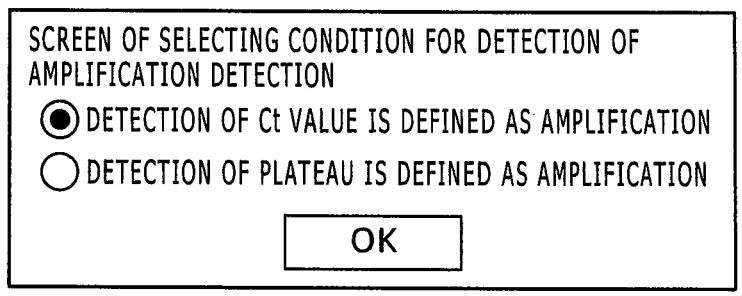
FIG. 7 is a view for explaining a screen of selecting conditions of detecting amplification in the first embodiment.

For judging detection of amplification in the genetic analyzer, detection of amplification is judged by the detection of the Ct value or the detection of the plateau. Alternatively, as shown in FIG. 7, it may be configured such that the user can select the condition for detecting the amplification based on the detection of the Ct value or the detection of the plateau before starting the analysis. Further, the Ct value detection method may be selected from the Crossing Point method or the 2nd Derivative Maximum method and, in the case of the Crossing Point method, a threshold value may be inputted.

Further, this genetic analyzer may be configured such that a user can register the conditions for terminating the amplification reaction before starting analysis. That is, this nucleic acid analysis apparatus can judge the presence or absence of amplification before a predetermined measurement completion time and, when the amplification is detected, can terminate the amplification reaction automatically in accordance with the conditions for terminating the amplification reaction registered before starting analysis. Thus, the user can select the optimal condition for terminating the amplification reaction and unnecessary amplification detection time can be shortened to improve throughput.

Further, the genetic analyzer may also be configured such that the conditions for terminating the amplification reaction can be set to the sample vessel, the reagent vessel, the reaction vessel, or a group of the reaction vessels collectively. Thus, the use can select the optimal condition for completing the amplification in accordance with the sample to be measured.

Second Embodiment

In this embodiment, when an amplification reaction is terminated, conditions for selecting the next processing are displayed on a screen, so that a user can select conditions of selecting the next processing.

FIG. 8 (A) illustrates an example of display on a screen of selecting conditions for next processing. The display screen displays conditions for selecting the next processing such that processing of Melting analysis or HRM analysis is performed, or thermal denaturation processing of deactivating an enzyme is performed, or a reaction vessel is discarded, so that a user can select desired next processing.

Other examples of conditions for selecting the next processing may also optionally include such combined conditions that a reaction vessel is transferred to a storage region, or subjected to thermal denaturation processing after the Melting analysis or HMR analysis, and it is discarded.

As a more preferred embodiment, as shown in FIG. 8 (B), an amplification detection condition 800 or a sample ID 801 may be displayed. In addition, sample information, reagent information, etc. may be displayed or can be referred to so long as the information belongs to a relevant reaction vessel.

Further, as shown in FIG. 8 (C), an amplification reaction curve 802 may also be displayed. Such information provides a reference to a user when selecting the conditions for selecting the next processing.

Further, in this genetic analyzer, a user can also register the conditions for selecting the next processing before starting analysis. That is, this nucleic acid analysis apparatus can automatically transfer to the next processing when the amplification reaction has been terminated in accordance with the conditions for selecting the next processing registered before starting analysis. Thus, only the next processing selection condition required for a user can be selected and unnecessary processing can be excluded to improve throughput.

Further, in this genetic analyzer, the conditions for selecting the next processing can be set to the sample vessel, the reagent vessel, the reaction vessel, or a group of the reaction vessels collectively. Thus, the user can select the optimal next processing in accordance with the sample to be measured.

Third Embodiment

In this embodiment, conditions for selecting next processing are held for every result of amplification reaction and the next processing is performed automatically in accordance with the result of the amplification reaction. The result of amplification reaction preferably includes at least detection of the Ct value, detection of the plateau, and no detection of amplification and, in addition, may also display information obtained by analyzing an amplification curve. It is preferred that the items shown in the second embodiment can be selected as conditions for selecting the next processing.

Further, as illustrated in FIG. 9, it is preferred that a user can register conditions for selecting the next processing for every result of the amplification reaction before starting amplification.

Further, in a more preferred embodiment, the conditions for terminating the amplification reaction are held, detection of amplification is judged before a predetermined measurement completion time, and the amplification reaction is terminated in accordance with the conditions for terminating the amplification detection when the amplification is detected. Further, it is preferred that a user can register the conditions for terminating the amplification reaction before starting the amplification as shown in the first embodiment.

Further, in this genetic analyzer, conditions for detecting the amplification, conditions for terminating the amplification reaction, and conditions of selecting the next processing for every result of amplification detection can be set to the sample vessel, the reagent vessel, the reaction vessel, or a group of the reaction vessels. As shown in FIG. 10, ID for specifying the reaction vessel is displayed an object 1000 for setting analysis conditions. Alternatively, the analysis condition setting object 1000 may be configured so that the reaction vessel can be selected in view of a selection box in the form of a list, etc. and the analysis condition setting object may be changed successively. Naturally, when the object 1000 for setting analysis conditions is changed, conditions of detecting the amplification, condition of amplification reaction, and conditions for selecting the next processing for every result of detection of the amplification are updated to the conditions of the object 1000 for setting analysis conditions being held. The sample vessel, the reaction vessel, or a group of the reaction vessels can be designated to the object 1000 for setting analysis conditions.

Thus, the user can select the optimal condition for terminating the amplification reaction and can select only the necessary next processing selection condition in accordance with a sample to be measured. Accordingly, analysis in which unnecessary amplification detection time is shortened and unnecessary processing is eliminated can be achieved to improve throughput in accordance with the necessity of the user.

Fourth Embodiment

In this embodiment, an embodiment of a nucleic acid amplification apparatus for practicing the first to third embodiments is to be described.

Figure 11:
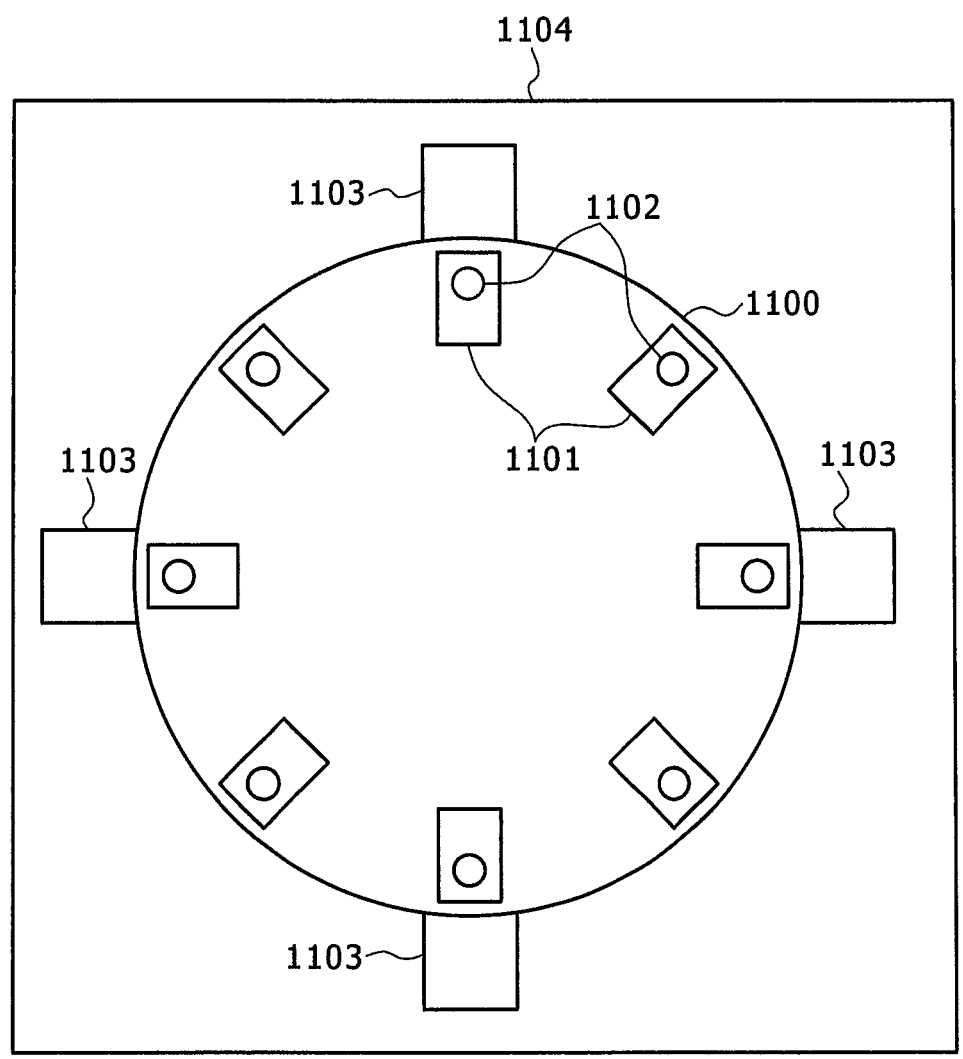
FIG. 11 is a view for explaining a nucleic acid amplification device in a fourth embodiment.

The nucleic acid amplification device illustrated in FIG. 11 has, on a holding unit base 1100, holding units 1102 provided with a plurality of temperature control blocks 1101 holding reaction vessels, fluorescence detectors 1103 for detecting fluorescence of a reaction solution contained in the reaction vessels, and a cover 1104 for covering the holding units 1102, and the fluorescent detectors 1103.

The temperature control block 1101 has a temperature control device including a Peltier element, a heat dissipation fin, and a temperature sensor and has a function of controlling the reaction vessel held on the holding unit 1102 at a predetermined temperature. The temperature and the timing for the change of temperature set in each of the temperature control blocks 1101 are controlled not depending on the temperature of the other temperature control blocks 1101.

The holding unit base 1100 has a rotatable structure although not illustrated. When the holding unit base 1100 rotates and the holding unit 1102 passes over each of the fluorescent detectors 1103, fluorescence of the reaction solution contained in the reaction vessel is detected.

A relative speed between the reaction vessel and the fluorescent detector 1103 can be controlled by controlling the rotational speed of the holding unit base 1100 to the fluorescent detector 1103 (relative rotational speed) upon measurement of fluorescence. The relative speed may be at a constant speed, or fluorescence can be detected at a position where the reaction vessel or the holding unit 1102 is opposed to the fluorescence detector 1103 while stopping them temporarily.

As described above, in the genetic analyzer having the nucleic acid amplification device provided with the temperature control device for every reaction vessel, processing for terminating the amplification reaction or next processing after the termination of the amplification reaction described in the first to third embodiments is performed to individual reaction vessels.

Further, the reaction vessel after termination of the amplification reaction is carried out by the robot arm device 112 and the gripper unit 113 from the nucleic acid amplification device and a new reaction vessel is carried into the nucleic acid amplification device. The new reaction vessel is newly provided with a temperature change (temperature cycle). By the provision of the temperature control device for every reaction vessel, analysis in the new reaction vessel can be started without depending on the situation of analysis in other reaction vessels to further improve the throughput.

Further, it can also be configured to perform continuous processing for the amplification processing, and processing of Melting analysis or HRM analysis, or thermal processing of deactivating an enzyme without movement of the reaction vessel.

Further in FIG. 11, a plurality of holding units 1102 may also be provided to the temperature control block 1101. In a case of a specific measurement vessel using an identical temperature reaction condition, throughput can be improved by continuous processing for Melting analysis or HRM analysis, or thermal processing after the termination of the amplification reaction for all the reaction vessels.

While the genetic analyzer of this invention has been described with reference to specific embodiments but the invention is not restricted to them. Persons skilled in the art can provide various modifications and improvements for the constitution and the function of the invention in each of the embodiments and other embodiments within a range not departing from the gist of the invention.

LIST OF REFERENCE SIGNS

100 genetic analyzer
101 sample vessel
102 sample vessel rack
103 reagent vessel
104 reagent vessel rack
105 reaction vessel
106 reaction vessel rack
107 reaction solution control position
108 capping unit
109 stirring unit
110 X axis of robot arm
111 Y axis of robot arm
112 robot arm device
113 gripper unit
114 dispensing unit
115 nozzle chip
116 nozzle chip rack
117 nucleic acid amplification device
118 discarding box
119 input section
120 display section
121 control section
200 fluorescence intensity calculation section
201 temperature cycle administration section
202 measurement time administration section
203 measured data administration section
204 amplification curve analysis section
205 amplification detection judging section
206 amplification termination judging section
300, 401 to 403, 407 amplification curve
301 lag phase
302 exponential phase
303 stationary phase
304 transition region between a lag phase and an exponential phase (Ct value detection point)
305, 404 to 406, 408 Ct value detection time
306 transition region between an exponential phase and a stationary phase (plateau detection point)
307 plateau detection time
308 measurement completion time
409 Ct value
500 to 507 steps in flow chart
600 input area 601, 800 amplification detection condition
602, 801 sample ID
603, 802 amplification reaction curve
1000 amplification condition setting object
1100 holding unit base
1101 temperature control block
1102 holding tool
1103 fluorescence detector
1104 cover

The invention claimed is:

1. A genetic analyzer for measuring and analyzing an amplification reaction of a nucleic acid in real time, comprising:
   a nucleic acid amplification device for conducting nucleic acid amplification and detecting fluorescence in the course of amplification;
   a control unit coupled to the nucleic acid amplification device;
   an input section coupled to the control unit;
   a display coupled to the control unit,
   wherein the control unit is programmed to display on the display a screen enabling selection, by the input section, of one of a plurality of analysis conditions of the nucleic acid amplification, which include:
   terminating an amplification reaction in which the amplification reaction is to be terminated instantly,
   continuing the amplification reaction until elapse of a measurement completion time and then terminating the amplification reaction, and
   continuing the amplification reaction until elapse of a predetermined time and then terminating the amplification reaction,
   wherein the nucleic acid amplification device includes a plurality of holding units disposed around a circumference of a disk that is rotatable and each holding unit has a temperature control block holding at least one reaction vessel containing a nucleic acid sample as a target for amplification processing and a reagent as a reaction solution,
   wherein each of the temperature control blocks is configured to control the temperature of the reaction solution and wherein the temperature control blocks are disposed apart from each other, and
   wherein the control unit is programmed to receive an input indicating a selection selected through the input section of one of the analysis conditions displayed on the screen for each nucleic acid sample contained in a reaction vessel, and the displayed analysis conditions are conditions for each nucleic acid sample for terminating the amplification reaction,
   wherein the control unit is further programmed to:
      control the nucleic acid amplification device to terminate the amplification reaction of a reaction solution according to the selected analysis condition corresponding to the sample in the reaction solution, and
      receive one or more inputs indicating selections selected through the input section of one of the analysis conditions displayed on the display screen for each of the nucleic acid samples before nucleic acid amplification of a nucleic acid sample is conducted by the nucleic acid amplification device.

2. The genetic analyzer according to claim 1, wherein said control unit is further programmed to process detection of an occurrence of the amplification reaction from a cycle threshold (Ct) value of the intensity of detected fluorescence.

3. The genetic analyzer according to claim 1, wherein said control unit is further programmed to process a detection of an occurrence of the amplification reaction from a plateau of the intensity of detected fluorescence.

4. The genetic analyzer according to claim 1, wherein said control unit is further programmed to process a detection of an occurrence of the amplification reaction from a cycle threshold (Ct) value or a plateau of the intensity of detected fluorescence, which a user can previously select.

5. The genetic analyzer according to claim 1, wherein said control unit is further programmed to process a detection of an occurrence of the amplification reaction from intensity of the detected fluorescence, and wherein the displayed analysis conditions to be selected by the user include conditions for detecting occurrence of the amplification reaction.

6. The genetic analyzer according to claim 1, wherein the control unit is further programmed to display an amplification reaction curve on the display.

7. The genetic analyzer according to claim 1, wherein the holding unit has a mechanism of successively carrying in the reaction vessels.

8. The genetic analyzer according to claim 1, wherein the holding unit has a mechanism of successively carrying out the reaction vessels.

9. The genetic analyzer according to claim 1, wherein the nucleic acid amplification device continuously performs the amplification reaction of the nucleic acid, processing of a Melting analysis or HRM analysis, or a thermal treatment of deactivating an enzyme without moving the reaction vessel.

10. The genetic analyzer according to claim 1, wherein the plurality of temperature control blocks are configured to control the temperature of the reaction solution independently from each other.

11. A genetic analyzer for measuring and analyzing an amplification reaction of a nucleic acid in real time, comprising:
    a nucleic acid amplification device for conducting nucleic acid amplification and detecting fluorescence in the course of amplification;
    a control unit coupled to the nucleic acid amplification device,
    wherein said control unit is programmed to process a detection of an occurrence of the amplification reaction from an intensity of the detected fluorescence,
    wherein the nucleic acid amplification device includes a plurality of holding units disposed around a circumference of a disk that is rotatable and each holding unit has a temperature control block holding one reaction vessel containing a nucleic acid sample as a target for amplification processing and a reagent as a reaction solution,
    wherein each of the temperature control blocks is configured to control the temperature of the reaction solution and are disposed apart from each other, and
    wherein the control unit is programmed to: when the occurrence of the amplification reaction has been detected before a predetermined measurement time has elapsed, processes predetermined user input that is a selection of analysis conditions which include conditions for terminating the amplification reaction, including:
    terminating the amplification reaction in which the amplification reaction is to be terminated instantly,
    continuing the amplification reaction until elapse of the measurement completion time and then terminating the amplification reaction, and
    continuing the amplification reaction until elapse of a predetermined time and then terminating the amplification reaction, and wherein said control unit is further programmed to:
control the nucleic acid amplification device to terminate the amplification reaction automatically in accordance with the predetermined condition for terminating the amplification reaction selected by the user, and
process one or more inputs indicating selections of the analysis conditions for each of the nucleic acid samples before nucleic acid amplification of a nucleic acid sample is conducted by the nucleic acid amplification device.

12. The genetic analyzer according to claim 11, further comprising reaction vessels for containing a nucleic acid sample as a target for amplification processing and a reagent, wherein the conditions for terminating the amplification reaction can be set for every reaction vessel.

13. The genetic analyzer according to claim 11, further comprising a display,
wherein the control unit is further programmed to display conditions for selecting a next processing and, when the amplification reaction is terminated, the control unit receives a section of a condition for selecting next processing through the input section.

14. The genetic analyzer according to claim 13, wherein said control unit is further programmed to process predetermined user input that sets the conditions for the next processing and, when the amplification reaction is terminated, the next processing is performed automatically in accordance with the predetermined conditions set for the next processing.

15. The genetic analyzer according to claim 14, further comprising reaction vessels for containing a nucleic acid sample as a target for amplification processing and a reagent, wherein the conditions for selecting the next processing can be set for every reaction vessel.

16. The genetic analyzer according to claim 13, wherein said control unit is further programmed to process a detection of an occurrence of the amplification reaction from intensity of the detected fluorescence, and display the conditions for selecting the next processing including a result of detection of the amplification reaction on the display.

17. The genetic analyzer according to claim 13, wherein the control unit is further programmed to display the conditions for selecting the next processing including an amplification reaction curve based on an intensity of the detected fluorescence on the display.

18. The genetic analyzer according to claim 13, wherein the control unit is further programmed to display conditions to be selected for a next processing including processing of Melting analysis or HRM analysis on the display.

19. The genetic analyzer according to claim 13, wherein the control unit is further programmed to display conditions to be selected for next processing including a thermal treatment of deactivating an enzyme on the display.

20. A genetic analyzer for measuring and analyzing an amplification reaction of a nucleic acid in real time, comprising:
a nucleic acid amplification device for conducting nucleic acid amplification and detecting fluorescence in the course of amplification;
a control unit coupled to the nucleic acid amplification device;
an input section coupled to the control unit;
a display coupled to the control unit, wherein the control unit is programmed to display on the display a screen enabling selection, by the input section, of one of a plurality of analysis conditions of the nuclei acid amplification, which include:
terminating the amplification reaction in which the amplification reaction is to be terminated instantly,
continuing the amplification reaction until elapse of the measurement completion time and then terminating the amplification reaction, and
continuing the amplification reaction until elapse of a predetermined time and then terminating the amplification reaction,
wherein the nucleic acid amplification device includes a plurality of holding units disposed around a circumference of a disk that is rotatable and each holding unit has a temperature control block holding at least one reaction vessel containing a nucleic acid sample as a target for amplification processing and a reagent as a reaction solution,
wherein each of the temperature control blocks is configured to control the temperature of the reaction solution independently from each other, and
wherein the control unit is programmed to receive an input indicating a selection selected through the input section of one of the analysis conditions displayed on the screen for each nucleic acid sample contained in a reaction vessel, and the displayed analysis conditions are conditions for each nucleic acid sample for terminating the amplification reaction
wherein the control unit is further programmed to:
control the nucleic acid amplification device to terminate the amplification reaction of a reaction solution according to the selected analysis condition corresponding to the sample in the reaction solution, and
receive one or more inputs indicating selections selected through the input section of one of the analysis conditions displayed on the display screen for each of the nucleic acid samples before nucleic acid amplification of a nucleic acid sample is conducted by the nucleic acid amplification device.

* * * * *